(12) United States Patent
Padmani et al.

(10) Patent No.: US 11,961,610 B2
(45) Date of Patent: Apr. 16, 2024

(54) DIGITAL COMMUNICATION MODULE FOR TRANSMISSION OF DATA FROM A MEDICAL DEVICE

(71) Applicants: Baxter International Inc., Deerfield, IL (US); Baxter Healthcare SA, Glattpark (CH)

(72) Inventors: Bhavesh S. Padmani, Hawthorn Woods, IL (US); Vithoba Hugar, Karnataka (IN); Vijaya Bhaskar Reddy Golla, Bangalore (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 240 days.

(21) Appl. No.: 17/211,151

(22) Filed: Mar. 24, 2021

(65) Prior Publication Data

US 2021/0304878 A1     Sep. 30, 2021

Related U.S. Application Data

(60) Provisional application No. 62/993,819, filed on Mar. 24, 2020.

(51) Int. Cl.
*G16H 40/20* (2018.01)
*G06F 9/445* (2018.01)
(Continued)

(52) U.S. Cl.
CPC ......... *G16H 40/20* (2018.01); *G06F 9/44505* (2013.01); *G16H 10/60* (2018.01);
(Continued)

(58) Field of Classification Search
CPC ........ G16H 40/20; G16H 10/60; G16H 20/40; G16H 30/20; G16H 40/40; G16H 40/67;
(Continued)

(56) References Cited

U.S. PATENT DOCUMENTS

| | | | |
|---|---|---|---|
| 6,664,893 | B1 | 12/2003 | Ereland et al. |
| 6,880,034 | B2 | 4/2005 | Manke et al. |

(Continued)

OTHER PUBLICATIONS

Written Opinion of the International Examining Authority for Application No. PCT/US2021/023878 dated Jan. 27, 2022.

*Primary Examiner* — Jason S Tiedeman
*Assistant Examiner* — Liza Tony Kanaan
(74) *Attorney, Agent, or Firm* — K&L Gates LLP

(57) ABSTRACT

A digital communication module for transmission of data from a medical device is disclosed. In an example, a digital communication apparatus includes an input interface configured for communicative coupling to a medical device and an output interface configured for communicative coupling to a medical network. A processor of the digital communication apparatus receives a configuration file that specifies one input port of the input interface and at least one output port of the output interface, a first data format, and a second data format. The processor installs drivers for the input and output ports specified by the configuration file, provisions the input interface with the specified input port to receive medical data from the medical device in the first data format, and provisions the output interface with the at least one specified output port to transmit the received medical data using the first data format and the second data format.

20 Claims, 8 Drawing Sheets

(51) Int. Cl.
*G16H 10/60* (2018.01)
*G16H 20/40* (2018.01)
*G16H 30/20* (2018.01)
*G16H 40/40* (2018.01)
*G16H 40/67* (2018.01)
*H04L 9/40* (2022.01)
*H04L 67/12* (2022.01)
*H04L 67/55* (2022.01)
*G06F 13/42* (2006.01)

(52) U.S. Cl.
CPC ............. *G16H 20/40* (2018.01); *G16H 30/20* (2018.01); *G16H 40/40* (2018.01); *G16H 40/67* (2018.01); *H04L 63/0421* (2013.01); *H04L 63/0428* (2013.01); *H04L 67/12* (2013.01); *H04L 67/55* (2022.05); *G06F 13/4282* (2013.01)

(58) Field of Classification Search
CPC ............. G06F 9/44505; G06F 13/4282; H04L 63/0421; H04L 63/0428; H04L 67/12; H04L 67/55; H04L 67/34; H04L 67/565; H04L 69/08
See application file for complete search history.

(56) References Cited

U.S. PATENT DOCUMENTS

| | | |
|---|---|---|
| 6,885,288 B2 | 4/2005 | Pincus |
| 7,300,418 B2 | 11/2007 | Zaleski |
| 7,316,658 B2 | 1/2008 | Kelly et al. |
| 7,595,723 B2 | 9/2009 | Heitzmann et al. |
| 7,645,258 B2 | 1/2010 | White et al. |
| 7,650,146 B2 | 1/2010 | Eberhart |
| 7,843,328 B2 | 11/2010 | Knauper |
| 7,933,780 B2 | 4/2011 | De La Huerga |
| 7,941,327 B2 | 5/2011 | Brown |
| 7,942,844 B2 | 5/2011 | Moberg et al. |
| 8,040,238 B2 | 10/2011 | Perkins |
| 8,082,160 B2 | 12/2011 | Collins, Jr. et al. |
| 8,095,692 B2 | 1/2012 | Mehta et al. |
| 8,105,282 B2 | 1/2012 | Susi et al. |
| 8,146,149 B2 | 3/2012 | Steinkogler et al. |
| 8,155,982 B2 | 4/2012 | Dicks et al. |
| 8,172,752 B2 | 5/2012 | Russ |
| 8,239,780 B2 | 8/2012 | Manetta et al. |
| 8,286,088 B2 | 10/2012 | Shaffer et al. |
| 8,444,595 B2 | 5/2013 | Brukalo et al. |
| 8,472,630 B2 | 6/2013 | Konrad et al. |
| 8,715,180 B2 | 5/2014 | Cohen et al. |
| 8,731,957 B2 | 5/2014 | Herbst et al. |
| 8,756,337 B1 | 6/2014 | Canion et al. |
| 8,769,625 B2 | 7/2014 | Wang et al. |
| 8,777,895 B2 | 7/2014 | Hsu et al. |
| 8,823,490 B2 | 9/2014 | Libbus et al. |
| 8,892,886 B2 | 11/2014 | Konrad et al. |
| 8,909,613 B2 | 12/2014 | Treu et al. |
| 8,924,458 B2 | 12/2014 | Levin et al. |
| 8,932,250 B2 | 1/2015 | Montgomery et al. |
| 8,945,043 B2 | 2/2015 | Lee et al. |
| 8,952,794 B2 | 2/2015 | Blomquist |
| 8,954,336 B2 | 2/2015 | Blomquist |
| 8,996,393 B2 | 3/2015 | Sobie |
| 9,123,077 B2 | 9/2015 | Silkaitis et al. |
| 9,143,941 B2 | 9/2015 | Wang et al. |
| 9,178,891 B2 | 11/2015 | Wang et al. |
| 9,338,819 B2 | 5/2016 | Meng et al. |
| 9,411,936 B2 | 8/2016 | Landrum et al. |
| 9,445,719 B2 | 9/2016 | Libbus et al. |
| 9,471,515 B2 | 10/2016 | Gao-Saari et al. |
| 9,471,752 B2 | 10/2016 | Goetz et al. |
| 9,483,615 B2 | 11/2016 | Roberts |
| 9,517,304 B2 | 12/2016 | Moberg et al. |
| 9,585,562 B2 | 3/2017 | Sobie |
| 9,619,621 B2 | 4/2017 | Dicks et al. |
| 9,635,111 B2 | 4/2017 | Wang et al. |
| 9,641,432 B2 | 5/2017 | Jha et al. |
| 9,773,060 B2 | 9/2017 | Gerst et al. |
| 9,792,660 B2 | 10/2017 | Cannon et al. |
| 9,800,663 B2 | 10/2017 | Arrizza |
| 9,889,257 B2 | 2/2018 | Mastrototaro et al. |
| 9,948,720 B2 | 4/2018 | Wang et al. |
| 10,026,504 B2 | 7/2018 | Schmoll et al. |
| 10,126,759 B2 | 11/2018 | Mueller |
| 10,185,834 B2 | 1/2019 | Adam et al. |
| 2003/0102836 A1* | 6/2003 | McCall ............... E05F 15/79 318/445 |
| 2007/0238010 A1* | 10/2007 | Zhang ............... H01M 8/023 429/491 |
| 2008/0218376 A1* | 9/2008 | Dicks ............... A61M 5/003 340/539.12 |
| 2010/0049005 A1* | 2/2010 | Espina Perez ....... A61B 5/0002 600/300 |
| 2010/0169120 A1 | 7/2010 | Herbst et al. |
| 2011/0219090 A1* | 9/2011 | Chan ............... G16H 40/67 709/206 |
| 2012/0011253 A1 | 1/2012 | Friedman et al. |
| 2012/0197973 A1* | 8/2012 | Tukol ............... G06F 9/4451 709/203 |
| 2012/0239824 A1 | 9/2012 | Nguyen et al. |
| 2013/0018355 A1 | 1/2013 | Brand et al. |
| 2014/0230071 A1 | 8/2014 | Adam et al. |
| 2015/0097697 A1* | 4/2015 | Laval ............... H04L 69/03 340/870.02 |
| 2015/0154369 A1 | 6/2015 | Blomquist |
| 2015/0205923 A1 | 7/2015 | Sobie |
| 2015/0207626 A1 | 7/2015 | Neftel et al. |
| 2015/0310182 A1 | 10/2015 | Henze et al. |
| 2016/0037145 A1 | 2/2016 | Tsukagoshi |
| 2016/0080365 A1 | 3/2016 | Baker et al. |
| 2017/0017786 A1 | 1/2017 | Siebert et al. |
| 2017/0220972 A1* | 8/2017 | Conway ......... G06Q 10/063118 |
| 2018/0032573 A1* | 2/2018 | Jarman ............... G16B 50/30 |
| 2019/0325353 A1* | 10/2019 | Aftab ............... G06F 8/30 |

* cited by examiner

DIGITAL COMMUNICATION MODULE FOR TRANSMISSION OF DATA FROM A MEDICAL DEVICE

PRIORITY CLAIM

This application claims priority to and the benefit as a non-provisional application of U.S. Provisional Patent Application No. 62/993,819, filed Mar. 24, 2020, the entire contents of which are hereby incorporated by reference and relied upon.

BACKGROUND

Medical networks typically have a significant number of connected medical devices. The networks receive data from the medical devices. After receiving the data, servers connected to the networks store the data to patient electronic medical records ("EMRs") or relay the data to certain hospital systems, such as a pharmacy system. For security, the data collected from the medical devices is only made available internally for user devices that have authorization to connect to the medical network. As a result of this network security, third-parties, such as medical device manufacturers, generally do not have access to the data that is generated by their deployed medical devices.

Some manufacturers attempt to obtain medical device data by having a sales representative or technician physically visit each medical device to remove at least some of the device data, including diagnostic information. However, this is an extremely labor intensive process. Additionally, this manual process oftentimes neglects or overlooks many medical devices from data collection due to the time and costs involved in the data collection. This can create gaps when the data is later analyzed. Further, this manual collection method is not timely since the data may only be analyzed days to weeks, or even months after collection.

Some other medical device manufacturers are granted limited access to medical device data that is stored within a medical network. In these instances, the device manufacturers have access to a data repository that is separate from patient records and hospital systems. One issue is that the data is limited to medical data that is transmitted from the medical device, and may not include data of interest to a manufacturer, such as diagnostic or usage information. Further, the data is formatted in a manner designated by the hospital system, which may make large-scale handling, processing, and analysis of the data difficult or impossible. Moreover, a device manufacturer with medical devices in tens to hundreds of different hospital systems (each with their own protocols and data storage requirements) would have to access each system separately and perform any data conversion to produce a uniform and useable data set.

The above-described issues deprive medical device manufacturers of valuable medical device data. For instance, device manufacturers could use the device data to address device issues, identify device operational trends, identify treatment trends, identify device operational recommendations, or help plan development of the next generation of devices. The lack of data oftentimes makes medical device manufactures reactive to issues rather than being proactive, which over the long term can impact the quality of patient treatment.

SUMMARY

A digital communication module ("DCM") for the transmission of data from a medical device is disclosed herein. The example DCM is positioned between a processor (or therapy module) of a medical device and a medical network. In some embodiments, the DCM is external to the medical device (connected via a serial connection or Ethernet connection). In other embodiments, the DCM is included within or integrated with a medical device. The DCM disclosed herein is configured as a gateway (such as an Internet of Things ("IoT") gateway) to transmit medical device data in parallel or simultaneously to a medical network and an external server (e.g., a medical device manufacturer server using an IoT shadow service) that is separate from the medical network.

In embodiments, the DCM receives medical device data from a processor or therapy module of a medical device. The DCM is configured to transmit two separate streams of the medical device data to the medical network. For a first data stream, the DCM provides the medical device data in a first format for transmission to an external server, which may be operated by a device manufacturer of the corresponding medical device. For a second data stream, the DCM provides the medical device data in a second format for transmission to EMR servers or hospital systems within the hospital network. In some instances, the DCM may de-identify the medical device data for the first data stream and add log/health data, which is of interest to the device manufacturer and permits advanced analytics to evaluate the operation of the medical devices. For the second data stream, the DCM transmits the medical device data with patient identifying information for inclusion into an appropriate EMR or for use by an appropriate hospital system. The DCM accordingly provides medical device manufacturers easy access to valuable medical device data in a common format for data analytics while also providing a hospital system the medical device data in the same format as used internally previously (thereby requiring no change to a medical network).

The example DCM disclosed herein may be configured remotely via a configuration file. The example file enables an operator to specify a medical device type, a hardware interface for connection to the medical device, device drivers for data management, a data transmission type, and hardware interfaces for data transmission. After receiving a configuration file, the DCM is configured to install specified drivers and configure the specified input and output interfaces to seamlessly integrate between a medical device and a medical network. The configuration file may be updated to change connectivity requirements and/or data formats to give device manufacturers flexibility after the DCM has been deployed at a hospital site.

The example DCM is operational with any type of medical device. For example, the DCM may operate with medical devices for plasmapherisis, hemodialysis ("HD"), hemofiltration ("HF") hemodiafiltration ("HDF"), and continuous renal replacement therapy ("CRRT") treatments. The DCM described herein may also operate with medical devices for peritoneal dialysis ("PD"), intravenous drug delivery, and nutritional fluid delivery. These different treatment modalities may be referred to herein collectively or generally individually as medical fluid delivery or treatment.

The above modalities may be provided by a medical fluid delivery machine that houses components needed to deliver medical fluid, such as one or more pumps, valves, heaters if needed, online medical fluid generation equipment if needed, sensors, such as pressure sensors, conductivity sensors, temperature sensors, air detectors, blood leak detectors, and the like, user interfaces, and control units, which may employ one or more processors and memory to control the above-described equipment. The medical fluid delivery machine may also include one or more filters, such as a dialyzer or hemofilter for cleansing blood and/or an ultrafilter for purifying water, dialysis fluid, or other fluid.

The DCM and the medical fluid delivery machine described herein may be used with home-based machines. For example, the systems may be used with home HD, HF or HDF machines, which are operated at the patient's convenience. One such home system is described in U.S. Pat. No. 8,029,454 ("the '454 patent"), issued Oct. 4, 2011, entitled "High Convection Home Hemodialysis/Hemofiltration And Sorbent System", filed Nov. 4, 2004, assigned to the assignees of the present application. Other such home systems are described in U.S. Pat. No. 8,393,690 ("the '690 patent"), issued Mar. 12, 2013, entitled "Enclosure for a Portable Hemodialysis System", filed Aug. 27, 2008. The entire contents of each of the above references are incorporated herein by reference and relied upon.

As described in detail below, the DCM of the present disclosure may operate within an encompassing platform system that may include many machines comprising many different types of devices, patients, clinicians, doctors, service personnel, electronic medical records ("EMR") databases, a website, a resource planning system handling data generated via the patient and clinician communications, and business intelligence. The DCM of the present disclosure operates seamlessly within the overall system and without contravening its rules and protocols.

In light of the disclosure herein and without limiting the disclosure in any way, in a first aspect of the present disclosure, which may be combined with any other aspect listed herein, a digital communication apparatus includes an input interface configured for communicative coupling to a medical device and an output interface configured for communicative coupling to a medical network. The input interface includes a serial input port, an Ethernet input port, and a wireless input port. The output interface includes at least one of a serial output port, an Ethernet output port, or a wireless output port. The digital communication apparatus also includes a memory device configured to store at least one configuration file and drivers for the input and output ports. The digital communication apparatus further includes a processor communicatively coupled to the input interface, the output interface, and the memory device. The processor is configured to receive a configuration file from an administration computer via the output interface, the configuration file specifying one of the input ports of the input interface and at least one output port of the output interface, a first data format, and a second data format. The processor is also configured to store the configuration file to the memory device, install drivers for the input and output ports specified by the configuration file, provision the input interface with the specified input port to receive medical data from the medical device in the first data format, and provision the output interface with the at least one specified output port to transmit at least some of the received medical data using the first data format and the second data format.

In a second aspect of the present disclosure, which may be combined with any other aspect listed herein, the processor is configured to receive the medical data in the first format from the medical device via the input interface, select a first subset of the medical data for transmission in the first data format via the output interface via one of the output ports as specified by the configuration file, convert a second subset of the medical data to the second data format, and transmit the second subset of the medical data in the second data format for transmission via the same or a different output port as specified by the configuration file.

In a third aspect of the present disclosure, which may be combined with any other aspect listed herein, the first subset of the medical data is the same as the second subset of the medical data.

In a fourth aspect of the present disclosure, which may be combined with any other aspect listed herein, the output interface provides for communicative coupling to at least one of an electronic medical record ("EMR") server, a middleware server, or an integration engine via the medical network, and the processor is configured to transmit the second subset of the medical data in the second data format to the at least one of the EMR server, the middleware server, or the integration engine using the same or the different output port as specified by the configuration file.

In a fifth aspect of the present disclosure, which may be combined with any other aspect listed herein, the at least one of the Ethernet port and the wireless port provide for communicative coupling to a remote server that is external to the medical network, and the processor is configured to transmit the first subset of the medical data in the first data format to the remote server using the at least one of the Ethernet port or the wireless port.

In a sixth aspect of the present disclosure, which may be combined with any other aspect listed herein, the processor includes a first connectivity agent and uses a messaging protocol for transmission of the first subset of the medical data in the first data format.

In a seventh aspect of the present disclosure, which may be combined with any other aspect listed herein, the messaging protocol includes a Message Queuing Telemetry Transport ("MQTT") publish-subscribe network protocol.

In an eighth aspect of the present disclosure, which may be combined with any other aspect listed herein, the configuration file specifies a first destination network address that is to receive the first subset of the medical data in the first data format, and specifies a second destination network address that is to receive the second subset of the medical data in the second data format, and the first destination network address is associated with a network domain that is external to the medical network and the second destination network address is associated with a network domain that includes the medical network.

In a ninth aspect of the present disclosure, which may be combined with any other aspect listed herein, the processor is configured to generate log data and health data include the log data and the health data with the first subset of the medical data for transmission in the first data format via the output interface via one of the output ports as specified by the configuration file, convert the log data to the second data format, and include the log data with the second subset of the medical data for transmission via the same or the different output port as specified by the configuration file.

In a tenth aspect of the present disclosure, which may be combined with any other aspect listed herein, the log data includes at least one of an identification of a medical device type, an identification of a medical device serial number, a time stamp from which the received medical data was generated by the medical device or received by the processor from the medical device, an identifier of the apparatus, a timestamp for the first subset of the medical data, or a monotonic time stamp, and the health information includes information related to the memory device, CPU usage information, network connectivity information, process/thread information, or information related to software operated by the processor for processing the first and second subsets of the medical data for transmission.

In an eleventh aspect of the present disclosure, which may be combined with any other aspect listed herein, the processor is configured to at least one of anonymize patient information included within the first subset of the medical data before transmission, or encrypt the first subset of the medical data before transmission.

In a twelfth aspect of the present disclosure, which may be combined with any other aspect listed herein, the processor is configured to receive a stream of the medial data, create a snapshot of the medical data at periodic intervals, and provide the snapshot of the medical data as at least one of the first subset of the medical data or the second subset of the medical data.

In a thirteenth aspect of the present disclosure, which may be combined with any other aspect listed herein, the periodic intervals have a period between five seconds and sixty seconds.

In a fourteenth aspect of the present disclosure, which may be combined with any other aspect listed herein, the processor is configured to use event tracking to identify changes to the medical data between snapshots, and include only the changed medical data from a previous snapshot as at least one of the first subset of the medical data or the second subset of the medical data.

In a fifteenth aspect of the present disclosure, which may be combined with any other aspect listed herein, the configuration file specifies a type of the medical device and that the medical data to be received from the medical device is provided in the first data format.

In a sixteenth aspect of the present disclosure, which may be combined with any other aspect listed herein, the type of medical device includes at least one of a continuous renal replacement therapy ("CRRT") machine, a peritoneal dialysis machine, a hemodialysis machine, a water purification machine, or a nutrition compounding machine.

In a seventeenth aspect of the present disclosure, which may be combined with any other aspect listed herein, the first data format includes JavaScript Object Notation ("JSON"), Hypertext Transfer Protocol ("HTTP"), or a binary protocol.

In an eighteenth aspect of the present disclosure, which may be combined with any other aspect listed herein, the second data format includes a Health-Level 7 ("HL7") protocol, a Fast Healthcare Interoperability Resources ("FHIR") protocol, or a binary protocol.

In a nineteenth aspect of the present disclosure, which may be combined with any other aspect listed herein, the wireless input port includes at least one of a Wi-Fi input port and a Bluetooth® input port and the wireless output port includes at least one of a Wi-Fi output port or a cellular output port.

In a twentieth aspect of the present disclosure, which may be combined with any other aspect listed herein, the medical data includes at least one of event information comprising transitions between fill, dwell, and drain phase of a dialysis cycle, alarm information, treatment programming information, or treatment information comprising an estimated fill rate, a drain rate, and an amount of ultrafiltration removed.

In a twenty-first aspect of the present disclosure, any of the structure and functionality disclosed in connection with FIGS. 1 to 9 may be combined with any of the other structure and functionality disclosed in connection with FIGS. 1 to 9.

In light of the present disclosure and the above aspects, it is therefore an advantage of the present disclosure to provide an improved system for conveying medical device data to medical device manufacturers.

It is another advantage of the present disclosure to use a configuration file to configure certain drivers and/or hardware interfaces on the DCM.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
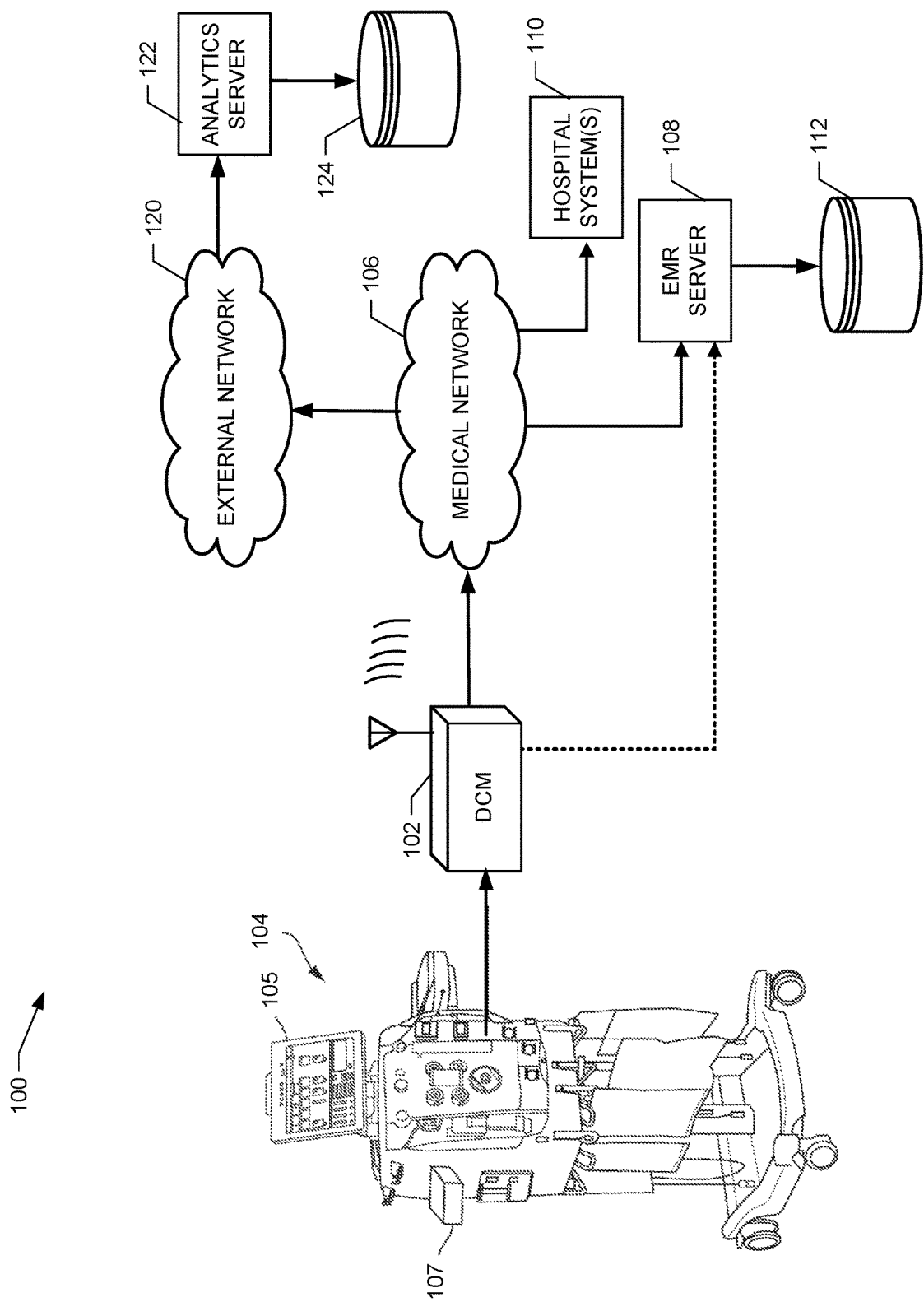
FIG. 1 is a diagram of a DCM environment including a DCM and a medical device, according to an example embodiment of the present disclosure.

A digital communication module ("DCM") for transmission of data from a medical device is disclosed. The example DCM is configured to receive medical device data from a medical device. The DCM transmits the medical device data in parallel to a local hospital network and an external server (such as a server of a medical device manufacturer). In some embodiments, the DCM de-identifies the medical device data that is transmitted to the external server. The DCM may also add health and/or log data to the medical device data transmitted to the external server. Further, in some embodiments, the DCM may convert the medical device data to a different format for the hospital system. The example DCM is provisioned via a configuration file that specifies input interface parameters, output interface parameters, device driver parameters, and/or data conversion parameters. After receipt of a configuration file, the DCM is configured to provision the specified input/output interfaces in addition to install specified device drivers and provision data conversion/encryption mechanisms.

The DCM is configured to operate with many different types of medical devices and communicate via different types of interfaces, such as a serial connection (e.g., an RS-232 or RS-485 connection), an Ethernet connection, a Wi-Fi connection, a Bluetooth® connection, and/or a universal serial bus ("USB") connection. The configurability of the DCM enables its use with many different types of medical devices, such as a peritoneal dialysis machine, a critical care dialysis machine, a continuous renal replacement therapy ("CRRT") machine, a hemodialysis machine, a water preparation/purification device, a nutrition compounding machine, an infusion pump, etc. Further, the configurability of the DCM enables its use within differently configured hospital systems. The configurability of the DCM accordingly enables medical device data to be transmitted to an external server without having to make connectivity or networking changes to medical devices or hospital systems.

Reference is made herein to medical device data. As disclosed, medical device data (e.g., medical data) is generated at a medical device and transmitted to the DCM. The medical device data includes treatment programming information, which comprises one or more parameters that define how a medical device is to operate to administer a treatment to a patient. For a peritoneal dialysis therapy, the parameters may specify an amount (or rate) of fresh dialysis fluid to be pumped into a peritoneal cavity of a patient, an amount of time the fluid is to remain in the patient's peritoneal cavity (i.e., a dwell time), and an amount (or rate) of used dialysis fluid and ultrafiltration ("UF") that is to be pumped or drained from the patient after the dwell period expires. For a treatment with multiple cycles, the parameters may specify the fill, dwell, and drain amounts for each cycle and the total number of cycles to be performed during the course of a treatment (where one treatment is provided per day or separate treatments are provided during the daytime and during nighttime). In addition, the parameters may specify dates/times/days (e.g., a schedule) in which treatments are to be administered by the medical fluid delivery machine. Further, parameters of a prescribed therapy may specify a total volume of dialysis fluid to be administered for each treatment in addition to a concentration level of the dialysis fluid, such as a dextrose level. For an infusion therapy, the parameters may include a volume to be infused, a medication to be infused, a medication concentration, a medication dosage, and/or an infusion rate.

The medical device data also includes event information that relates to administration of the treatment. The event information may include data generated by a medical device that is indicative of measured, detected, or determined parameter values. For example, while a prescribed therapy may specify that a treatment is to comprise five separate cycles, each with a 45 minute dwell time, a medical fluid delivery device may administer a treatment where fewer cycles are provided, each with a 30 minute dwell time. The medical device monitors how the treatment is administered and accordingly provides parameters that are indicative of the operation. The parameters for the treatment data may include, for example, a total amount of dialysis fluid administered to the patient, a number of cycles operated, a fill amount per cycle, a dwell time per cycle, a drain time/ amount per cycle, an estimated amount of UF removed, a treatment start time/date, and/or a treatment end time/date. The treatment data may also include calculated parameters, such as a fill rate and a drain rate, determined by dividing the amount of fluid pumped by the time spent pumping. The treatment/event data may further include an identification of an alarm that occurred during a treatment, a duration of the alarm, a time of the alarm, an event associated with the alarm, and/or an indication as to whether the issue that caused the alarm was resolved or whether the alarm was silenced.

The medical device data further includes device machine logs that include diagnostic information, fault information, etc. The diagnostic information may include information indicative of internal operations of a medical device, such as faults related to pump operation, signal errors, communication errors, software issues, etc. The medical device data may be transmitted as a data stream or provided at periodic intervals. In some instances, the medical device data may be transmitted as events or other changes to the data occur.

Reference is also made herein to log data and health data that is generated by the example DCM. The log data includes an identification of a therapy (medical) device type, identification of a therapy device serial number, a timestamp from which the treatment data was generated or received from the therapy device, an identifier of the DCM, a timestamp for the snapshot, and/or a DCM monotonic timestamp. The health information includes, for example, DCM system memory information, DCM central processing unit ("CPU") usage information, network connectivity information, process/ thread information, and information regarding embedded software applications.

While the following shows a DCM that partitions medical device data into two separate data streams or subsets, it should be appreciated that the DCM may partition the data into three or more separate streams. In some examples, each different stream may be directed to a different destination, include a different data format, and/or include different subsets of medical device data and/or log/health data. In addition to an analytics server of a manufacturer, the medical device data may be provided to a data analytics server of a pharmaceutical/dialysis fluid manufacturer, a continuous quality improvement system, an auditor, a regulator, etc.

I. DCM ENVIRONMENT EMBODIMENT

FIG. 1 is a diagram of a DCM environment 100, according to an example embodiment of the present disclosure. The example DCM environment 100 includes at least one DCM 102 communicatively coupled to a medical device 104. The DCM 102 may be connected to the medical device 104 via a serial connection, an Ethernet connection, a USB connection, a Wi-Fi connection, a Bluetooth® connection, etc. The example DCM 102 may include a network gateway, such as an IoT gateway.

In the example embodiment, the DCM 102 is configured to only receive medical device data from the medical device 104. This uni-directional communication configuration prevents another device from being able to access, program, or otherwise communicate with the medical device 104 via the DCM 102. However, in some embodiments, the DCM 102 may have a bi-directional communication link with the medical device 104 to enable data, programming instructions, or information to be transmitted to the medical device. While only one DCM 102 and medical device 104 are shown in FIG. 1, it should be appreciated that the environment 100 may include tens to hundreds or thousands of medical devices and respective DCMs.

The example medical device 104 is configured to accept one or more parameters specifying a treatment or prescription (i.e., treatment programming information). During operation, the medical device 104 writes event, diagnostic, and/or operational data to one or more log files. In some embodiments, the medical device 104 may store medical device data to a log file periodically, such as every five seconds to sixty seconds and/or after there is a change in data. The new medical device data written to the log file is transmitted to the DCM 102. In some embodiments, the medical device 104 creates the medical device data in a JavaScript Object Notation ("JSON") format, a HyperText Markup Language ("HTML") format, an Extensible Markup Language ("XML") format, a comma-separated values ("CSV") format, a text format, and/or a Health-Level-7 ("HL7") format.

The example medical device 104 may include one or more control interfaces 105 for displaying instructions and receiving control inputs from a user. The control interface 105 may include buttons, a control panel, or a touchscreen. The control interface 105 may also be configured to enable a user to navigate to a certain window or user interface on a screen of the medical device 104. The control interface 105 may also provide instructions for operating or controlling the medical device 104.

The example medical device 104 also includes a processor or therapy module 107. The processor or therapy module 107 of the medical device 104 operates according to one or more instructions for performing a treatment on a patient. The instructions may be acquired via the control interface 105. The processor or therapy module 107 also monitors device components for issues, which are documented as diagnostic information. The processor or therapy module 107 creates medical device data in conjunction with operating one or more pumps or other components to administer the treatment. The processor or therapy module 107 transmits the medical device data to the DCM 102.

The example DCM environment 100 also includes a medical network 106, which communicatively couples the DCM 102 to an EMR server 108 and one or more hospital systems 110. The medical network 106 can include any number of gateways, routers, system hubs, switches, and/or network appliances for establishing communication connections and routing data. The medical network 106 may include one or more firewalls that restrict access to only authorized remote devices and/or servers. The medical network 106 may include any local area network ("LAN"), Ethernet network, Wi-Fi network, or combinations thereof.

As shown in FIG. 1, the DCM 102 may be wired or wirelessly coupled to the medical network 106. In some embodiments, the connection may include an Ethernet connection, a Wi-Fi connection, and/or a cellular connection. Additionally or alternatively, the DCM 102 may have a serial connection to the EMR server 108 (or the hospital system 110) that bypasses the medical network 106.

Figure 2:
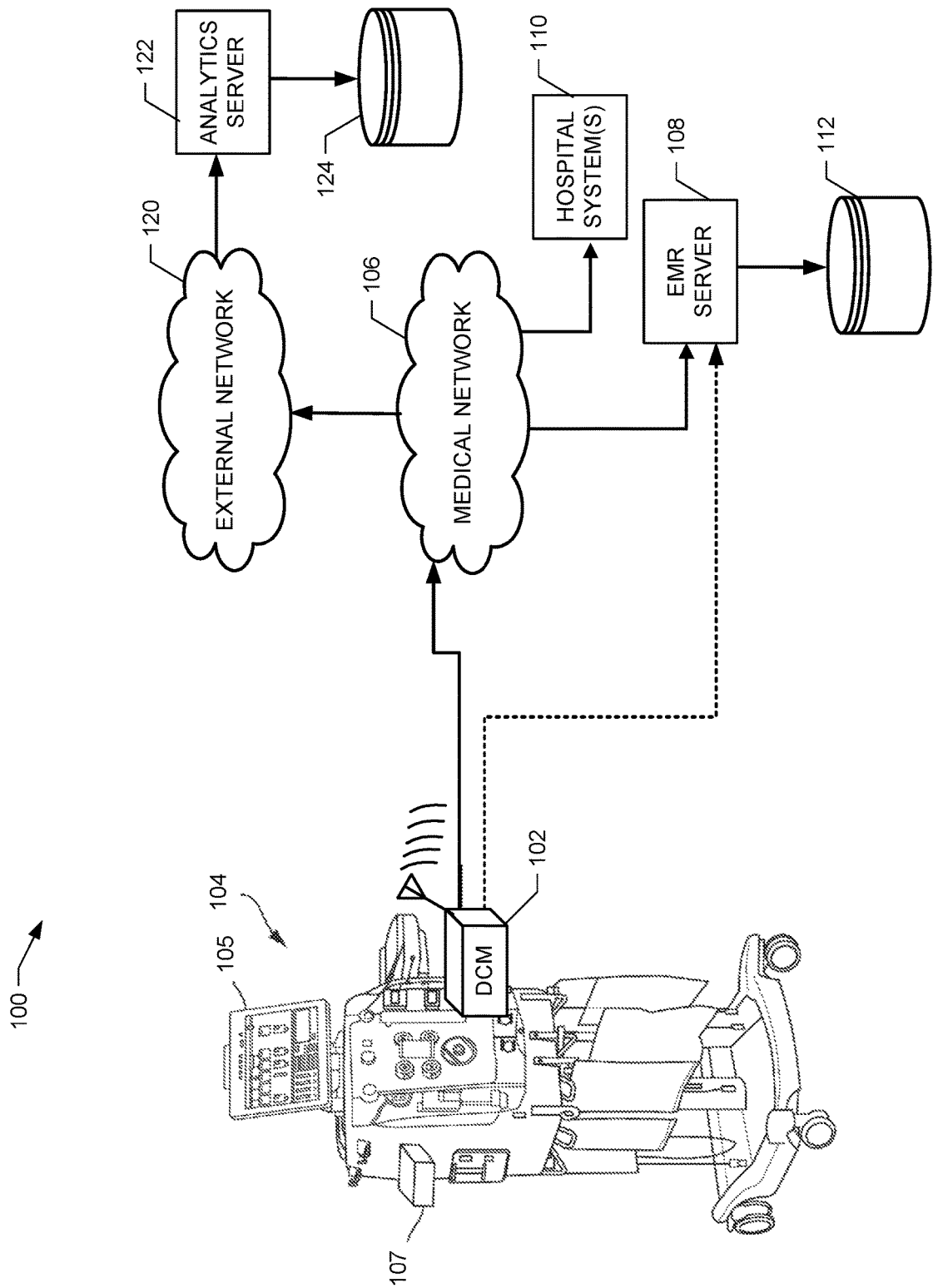
FIG. 2 is another diagram of the DCM environment, according to an example embodiment of the present disclosure.

FIG. 2 is another diagram of the DCM environment 100, according to an example embodiment of the present disclosure. In this embodiment, the DCM 102 is included within and/or integrated with the medical device 104. The DCM 102 may include, for example, a Digi ConnectCore® 6UL module, which has a NXP i.MX6UL-2, Cortex-A7 528 MHz CPU and 256 MB/1 GB NAND and DDR3 flash drives. The DCM 102 may be connected to a communication bus of the medical device 104 for receiving medical device data. The DCM 102 (including the DCM of FIG. 1) also includes an 802.11a/b/g/n/ac Wi-Fi radio and/or a Bluetooth® 4.2 radio. The DCM 102 may include a Yocto Linux operating system and contains drivers for the Digi chipset.

The example EMR server 108 of FIGS. 1 and 2 is configured to manage patient EMRs that are stored in a database of a memory device 112. The EMR server 108 is configured to receive medical device data, parse the data based on patient identifier, locate corresponding patient EMRs in the memory device 112, and store the parsed medical device data to the identified EMR. The EMR server 108 may also access one or more EMRs in response to request messages that identify the respective patients. The EMR server 108 may store the medical device data in a HL7 format, a binary version 2 format, a binary version 3 format, or a Fast Healthcare Interoperability Resources ("FHIR") format.

The example DCM environment 100 may include any of a service portal, an enterprise resource planning system, a web portal, a business intelligence portal, a HIPAA compliant database, a pharmacy system, etc. The DCM environment 100 may also include a middleware system and/or an integration engine. The DCM environment 100 enables user devices (e.g., smartphones, laptop computers, workstations, tablet computers, etc.) to read and/or write to the medical device data stored in the EMRs of the memory device 112.

The example DCM environment 100 of FIG. 1 also includes an external network 120 that is communicatively coupled to an analytics server 122. The external network 120 may include any routers, gateways, switches, cellular towers, and/or network appliances for routing data over a wide area network ("WAN") such as the Internet, a cellular network (e.g., a 4G, 5G, or 6G cellular network), or combinations thereof. The external network 120 is communicatively coupled to the medical network 106 via one or more Ethernet and/or cellular connections. The medical network 106 may be assigned a domain address or sub-domain address, which is recognized by the external network 120 for routing data to and/or from devices connected to the medical network 106. In some embodiments, a cellular connection of the DCM 102 may bypass the medical network 106 and instead couple to a cellular network of the external network 120.

The example analytics server 122 is configured to receive at least some medical device data from the DCM 102. The analytics server 122 stores the received data to a memory device 124, which may include any device configured for persistent storage of data. The memory device 124 operates with the analytics server 122 to store medical device data via Amazon Web Services® ("AWS") through a Platform as a Service ("PaaS") framework. In other embodiments, the memory device 124 may be configured to store the medical device data in a Structured Query Language ("SQL") database, a NoSQL database, an Amazon® Relational Database Service ("RDS"), etc. The analytics server 122 may include one or more application programming interfaces ("API") configured for receiving the medical device data from the DCM 102. The APIs may be connected to ports at the analytics server 122 that are assigned one or more destination Internet Protocol ("IP") addresses. The DCM 102 is configured with the one or more destination IP addresses to enable transmission of medical device data to the analytics server 122.

The analytics server 122 is configured to periodically analyze the received medical device data for certain key performance indicators ("KPIs") related to operation of the medical device 104. The KPIs may be related to treatment trends, component (e.g., pump or filter) usage, alert/alarm trends, etc. The analytics server 122 may analyze the medical device data to determine recommendations and/or guidelines to improve operation of the medical device 104 and/or improve treatment protocols for certain disease conditions. For example, the analytics server 122 may determine more optimal peritoneal dialysis programming parameters for patients that have a certain degree of kidney failure. The analysis of the medical device data may include the analytics server 122 providing standardization, parsing of DCM device logs, and analysis of DCM health statistics.

In the illustrated example, the medical device 104 is the PrisMax CRRT machine manufactured by Baxter International Inc. It should be appreciated that in other embodiments, the medical device 104 may include any other renal failure therapy machine, infusion pump, physiological sensor, etc. The medical device 104 may include, for example, an infusion pump (e.g., a syringe pump, a linear peristaltic pump, a large volume pump ("LVP"), an ambulatory pump, multi-channel pump), a nutritional compounding machine, an oxygen sensor, a respiratory monitor, a glucose meter, a blood pressure monitor, an electrocardiogram ("ECG") monitor, a weight scale, and/or a heart rate monitor.

Regarding renal failure therapy machines, due to various causes, a patient's renal system can fail. Renal failure produces several physiological derangements. For instance, a patient experiencing renal failure can no longer balance water and minerals or excrete daily metabolic load. Toxic end products of nitrogen metabolism (urea, creatinine, uric acid, and others) can accumulate in the patient's blood and tissue. Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

II. DCM EMBODIMENT

Figure 3:
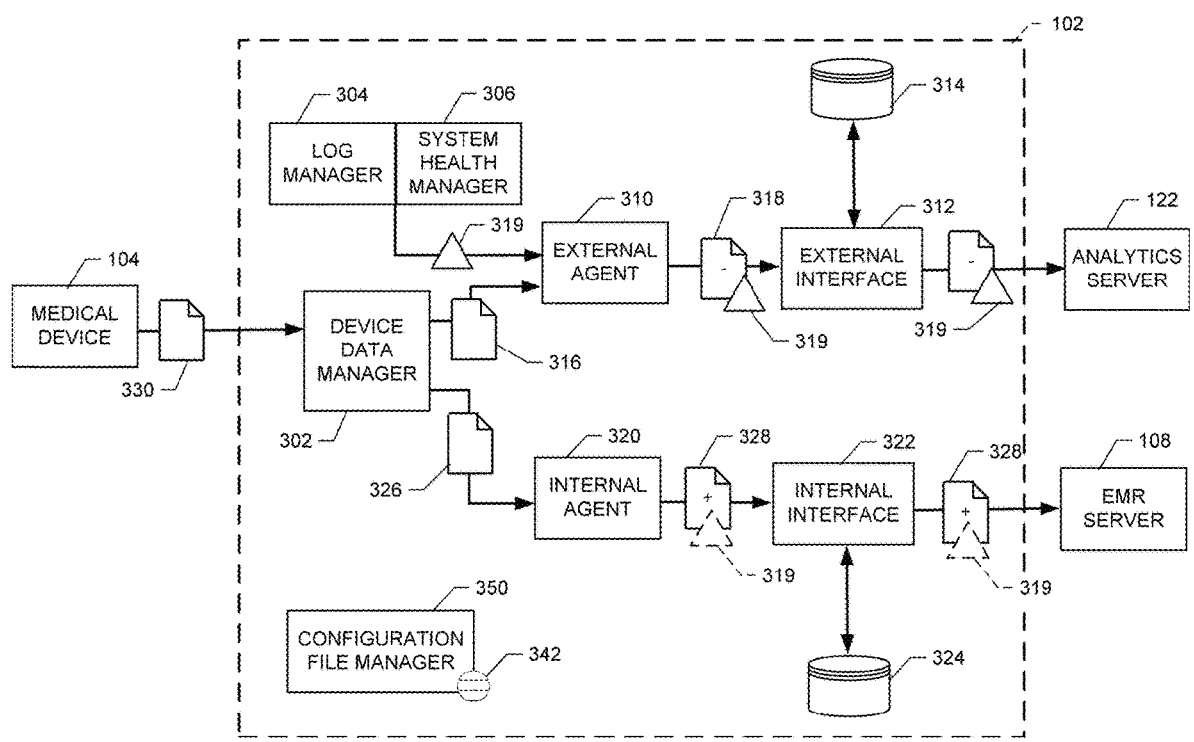
FIG. 3 is a diagram of the example DCM of FIGS. 1 and 2, according to an example embodiment of the present disclosure.

FIG. 3 is a diagram of the example DCM 102 of FIGS. 1 and 2, according to an example embodiment of the present disclosure. The example DCM 102 includes a data device manager 302 that is configured to generate two parallel data steams for medical device data received from a medical device 104. The DCM 102 also includes a log manager 304 and a system health monitor 306 to acquire or provide information related to the DCM. For a first data stream or subset provided to the analytics server 122, the DCM 102 includes an external agent 310, an external interface 312, and an external persistent storage device 314. For a second data stream or subset provided to the EMR server 108, the DCM 102 includes an internal agent 320, an internal interface 322, and an internal persistent storage device 324.

The example components 302 to 312, 320, and 322 of the DCM may be implemented using one or more computer programs or applications. The programs or the applications may be defined by a series of computer instructions that are stored on any computer-readable medium, including random access memory ("RAM"), read only memory ("ROM"), flash memory, magnetic or optical disks, optical memory, or other storage media. The instructions may be configured to be executed by a processor of the DCM 102, which when executing the series of computer instructions performs or facilitates the performance of all or part of the disclosed methods and procedures disclosed herein. The persistent storage devices 314 and 324 may include any memory device including RAM, ROM, flash memory, etc.

The example data device manager 302 is configured to interface with the medical device 104 for receiving the medical device data. The data device manager 302 is configured to create a snapshot of the medical device data at discrete points of time. The time periods may be specified by a configuration file (such as configuration file 342) and include, for example, five second intervals, ten second intervals, thirty second intervals, sixty second intervals, etc. For each snapshot the data device manager 302 reads the most recent received data from the medical device 104. In this manner, the device data manager 302 provides periodic updates regarding a status of the medical device 104.

In an example, the medical device 104 may transmit medical device data 330 in a continuous stream, periodic intervals, or after changes to the data. The medical device 104 may transmit the medical device data 330 in a log file or a stream of messages. The device data manager 302 compiles the received data since the last snapshot interval. When the next interval approaches, the device data manager 302 compiles the most recent data of the compilation into the snapshot to provide a representation of the medical device 104 at that point in time. If multiple events occur during a compilation period, the device data manager 302 may include only the most recent event or all of the events that occurred during the time period.

In some instances, the device data manager 302 may compare a current snapshot to a previous snapshot. Based on the comparison, the device data manager 302 may only include medical device data in the current snapshot that has changed since the previous snapshot. The comparison reduces the amount of data transmitted in each snapshot such that only new and/or updated medical device data 330 is communicated. For example, a CRRT medical device 104 may continuous transmit an estimated UF removed value, which typically does not change during fill and dwell cycles of a PD treatment. As such, the device data manager 302 only includes the UF removed value when there are changes to the value. In another example, an alarm may activate at a certain time. A device status may be included in the medical device data 330 that is indicative that the alarm is still active. However, the device data manager 302 only includes a notice in a first snapshot of a time the alarm activate (and a an alarm type) and a time the alarm was silenced or reset in a second subsequent snapshot, without including indications that the alarm was active in the intermediate snapshots.

In other embodiments, the medical device 104 may selectively only transmit medical device data that has changed from previous values or reflect a new event. In these instances, the device data manager 302 writes the received medical device data 302 to the appropriate snapshot.

In conjunction with creating a snapshot of the medical device data 330, the example device data manager 302 creates two separate data sets or streams. A first data set or stream 316 is for the analytics server 122. A second data subset or stream 326 is for the EMR server 108 and/or the hospital system 110. The first data stream or subset 316 may include the same medical device data 330 from the snapshot as the second data stream or subset 326. In other embodiments, the may include additional or fewer medical device data 330 from the snapshot compared to the second data stream or subset 326. For instance, the device data manager 302 may be configured to include diagnostic data (identified by metadata, data field label, placement, etc.) in the first data stream or subset 316 while not including the diagnostic data in the second data stream or subset 326. Further, the device manager 302 may include patient-identifying data in the second data stream or subset 326 while not including any patient-identifying data in the first data stream or subset 316.

The example DCM 102 includes the external agent 310 for de-identifying the first data stream or subset 316 to generate a de-identified first data stream or subset 318. The external agent 310 may be configured to search for data labels or keywords that are indicative of patient names, hospital-assigned identifiers, social security number, etc. In some instances, the patient-specific information may be replaced with a (randomly) generated session identifier that is used by the analytics server 122 to associate medical device data from the same treatment. In other embodiments, the patient-identifying information is removed or deleted by the external agent 310.

The example external agent 310 is also configured to combine or include log and/or health data 319 with the de-identified first data stream or subset 318. The log data is generated by the log manager 304 and includes an identification of a medical device type, identification of a medical device serial number, a timestamp from which the medical device data 330 was generated or received from the medical device 104, an identifier of the DCM 102, a timestamp for the snapshot created by the device data manager 302, and a DCM monotonic timestamp. The identification of a medical device type, identification of a medical device serial number, and identifier of the DCM 102 may be specified in the configuration file 342. In some instances, the identification of a medical device type and the identification of a medical device serial number may be reported by the medical device 104. The log manager 304 is configured to store this information create the appropriate timestamps as the medical device data 330 is received and/or the snapshots are created. The log manager 304 then transmits the log data to the external agent 310 for each snapshot corresponding to the de-identified first data stream or subset 318 that is transmitted to the analytics server 122.

The example system health manager 306 is configured to acquire and/or determine health information relayed to the DCM 102. The system health manager 306 is configured to transmit to the external agent 310 DCM system memory information (related to the persistent storage devices 314 and 324), DCM CPU usage information, network connectivity information, process/thread information, and/or information related to one or more software applications operating on the DCM 102. To acquire this information, the system health manager 306 is configured to access and/or read memory usage information of the persistent storage devices 314 and 324. Further, the system health manager 306 is configured to monitor one or more processors of the DCM 102 that implement the operations described herein. The system health monitor 306 also monitors network connections and/or detects loss of network connections via lack of reception of acknowledgement messages with the analytics server 122 and/or the EMR server 108. Similar to the log manager 304, the system health manager 306 transmits the health information to the external agent 310 for transmission with the de-identified first data stream or subset 318. In some instances, the configuration file 342 may specify which information is to be acquired by the system health monitor 306 and/or specify which of the health information is to be provided to the external agent 310 and/or the internal agent 320.

The example external agent 310 configures the de-identified first data stream or subset 318 and/or the log/health data 319 for transmission to the analytics server 122. The external agent 310 receives a destination IP address of the analytics server 122 from the configuration file 342. The external agent 310 may also receive domain connectivity information for the medical network 106 and/or API connection information for the analytics server 122 from the configuration file 342. The external agent 310 creates one or more messages with the de-identified first data stream or subset 318 and/or the log/health data 319 for transmission to the analytics server 122 using the destination address and networking domain information provided by configuration file 342.

In some embodiments, the external agent 310 encrypts the one or more messages including the de-identified first data stream or subset 318 and/or the log/health data 319. The external agent 310 may use an encryption protocol and/or private key that is specified by or provided by the configuration file 342. For example, the configuration file 342 may specify that the external agent 310 is configured to use transport layer security ("TLS") and/or using AES 256 GCM cypher for encryption. The external agent transmits the (encrypted) messages to the external interface 312.

In some embodiments, the external interface 312 (and/or the internal interface 322) is configured to use MQ Telemetry Transport ("MQTT") for transmitting messages with the de-identified first data stream or subset 318 and/or the log/health data 319 to the analytics server 122. In this instance, the external interface 312 is configured as a publisher and the analytics server 122 is configured as a broker. In other examples, the internal interface 312 (and/or the internal interface 322) may be configured to communicate using Minimum Lower Layer Protocol ("MLLP").

In some instances, the example external interface 312 is configured to determine if an active connection to the analytics server 122 exists. The external interface 312 may transmit periodic pings to the analytics server 122 to determine a network status based on a response to the pings. In other examples, the external interface 312 may determine if an acknowledgement message is received in response to the transmission of a snapshot of de-identified first data stream or subset 318 and/or the log/health data 319. If an acknowledgement message is not received within a specified threshold, the external interface 312 determines a loss of a network connection has occurred with the analytics server 122. After determining that a connection to the analytics server 122 does not exist, the external interface 312 is configured to store the encrypted messages containing the de-identified first data stream or subset 318 and/or the log/health data 319 to the external persistent memory device 314. The external interface 312 stores subsequent snapshots of messages containing the de-identified first data stream or subset 318 and/or the log/health data 319 to the memory device 314 until a network connection is reestablished. At that point, the external interface 312 transmits all of the stored messages in the memory device 314 to the analytics server 122.

In some instances, a connection with the analytics server 122 is not established. In these examples, the external interface 312 is configured to store the de-identified first data stream or subset 318 and/or the log/health data 319 to the memory device 314 until the data can be retrieved manually by an operator connecting a computer or USB memory device to the DCM 102. The external interface 312 may be configured, by the configuration file 342, to store a specified number of hours or days of data. After the specified number of hours or days has elapsed, the external interface 312 may overwrite the oldest data with newly received data.

If a connection to the analytics server 122 is present, the external interface 312 transmits one or more messages with the de-identified first data stream or subset 318 and/or the log/health data 319 to the analytics server 122 (e.g., a specified API at a designated IP address). In some embodiments, the external interface 312 may perform an automatic authentication with the analytics server 122 before the de-identified first data stream or subset 318 and/or the log/health data 319 may be transmitted. In an example, the configuration file 342 may include authentication information including, for example, an identifier of the DCM 102 and/or a unique password for the DCM 102. The external interface 312 first transmits the authentication information to the analytics interface 122. After receiving an acceptance message from the analytics server 122, the external interface transmits the transmits one or more messages with the de-identified first data stream or subset 318 and/or the log/health data 319 to the analytics server 122. In some instances, the external interface 312 uses the authentication information to establish a session with the analytics server 122. During this session, the external interface 312 may transmit subsequent snapshots of the de-identified first data stream or subset 318 and/or the log/health data 319 to the analytics server 122 without having to re-authenticate. The session may timeout if data is not received within a specified time period, such as five minutes.

In addition to transmitting the de-identified first data stream or subset 318 and/or the log/health data 319 to the analytics server 122, the DCM 102 also transmits the second data stream or subset 326 to the EMR server 108. As shown in FIG. 3, the device data manager 302 transmits the second data stream or subset 326 to the internal agent 320. Each transmission may comprise a snapshot of the second data stream or subset 326.

In some embodiments, the internal agent 320 is communicatively coupled to the log manager 304 and/or the system health manager 306. In these embodiments, the internal agent receives at least some of the log/health data 319 that is provided to the external agent 310. For instance, the internal agent may receive, from the log manager 304, information indicative of the medical device type, a serial number of the medical device, and/or a timestamp from which the medical device data was generated or received from the medical device 104. The internal agent combines the log data 319, for example, with the second data stream or subset 326. In other embodiments, the internal agent 320 does not receive any log/health data 319.

After combining any log/health data 319 with the second data stream or subset 326, the internal agent 320 is configured to format the data into a data format that is compatible with or needed by the EMR server 108. In other words, the internal agent creates a conversion of second data stream or subset 328 and/or the log data 319. The conversion type may be specified by the configuration file 342. The conversion may be, from, for example, JSON to HL7, binary, and/or FHIR. The internal agent 320 may include one or more files and/or algorithms that specifies how, for example, second data stream or subset 326 and/or the log data 319 in a JSON format is to be converted into HL7, binary, and/or FHIR. The file and/or algorithm may identify JSON data by position, data label, field name, and/or metadata and specify how the data is to be converted, including conversion of data label names, metadata names, numeric format, positioning, etc.

The internal agent 320 then transmits the converted second data stream or subset 328 and/or the log data 319 to the internal interface 322.

The example internal interface 322 is configured to check for a connection to the EMR server 108 in a similar manner as the external interface 312 checks for a connection with the analytics server 122. Additionally for serial connections, the internal interface 322 may check for the presence of a serial connector into a port of the DCM 102. If a connection is not present, the internal interface 322 stores the converted second data stream or subset 328 and/or the log data 319 to the internal persistent memory device 324. If a connection is present, the internal interface 322 transmits one or more messages with the second data stream or subset 328 and/or the log data 319 to the EMR server 108 (including any previously stored messages in the memory device 324 with previous snapshots of the second data stream or subset 326 and/or the log data 319). In some embodiments, the internal interfere 322 may encrypt the messages (for non-serial connections) with the converted second data stream or subset 328 and/or the log data 319 if the EMR server 108 supports conversion.

The example DCM 102 of FIG. 3 also includes a configuration file manager 350 for storing and/or processing one or more configuration files 342. The configuration file manager 350 is configured to receive and a configuration file 342 from a computer 400 or a server 500, as discussed below in connection with FIGS. 4 and 5.

The configuration file manager 350 reads the configuration file 342 and configures the log manager 304, the system health manager 306, the device data manager 302, the external agent 310, the external interface 312, the internal agent 320, and/or the internal interface 322 as specified in the file 342. For the log manager 304, this may include writing a DCM identifier, medical device type, medical device identifier, etc. to registers, parameters/or variables of the log manager 304. For the system health manager 306, that may include specifying parameters/attributes of the memory devices 314, 324 and/or a processor/CPU of the DCM 102 to monitor. For the internal agent 320, this may include specifying a data type for conversion.

In some instances, the configuration file manager 350 may also specify a conversion file type for the external agent 310. Further, the configuration file manager 350 configures the device data manager 302 based on a duration between snapshots, types of medical device data to be included in the separate streams and/or subsets 316, 326 and/or a type of data that is to be received from the medical device 104 (e.g., JSON data, HTML data, binary data, HL7 data, XML data, etc.). The configuration file manager 350 also reads the configuration file 342 to specify network credentials, authentication information, encryption keys, API identifiers, destination IP addresses, etc. for the external interface 312 and the internal interface 322.

The configuration file manager 350 may also define or otherwise provide a user interface that enables a user of the computer 600 or the server 700 to view and/or modify a stored configuration file 342. The user interface may include fields for configuring a network connection of the DCM 102, specifying an identifier of the DCM 102, specifying a username/password to access the DCM 102, specifying parameters of the configuration file 342, and/or installing software, such as a connectivity client or application.

Figure 4:
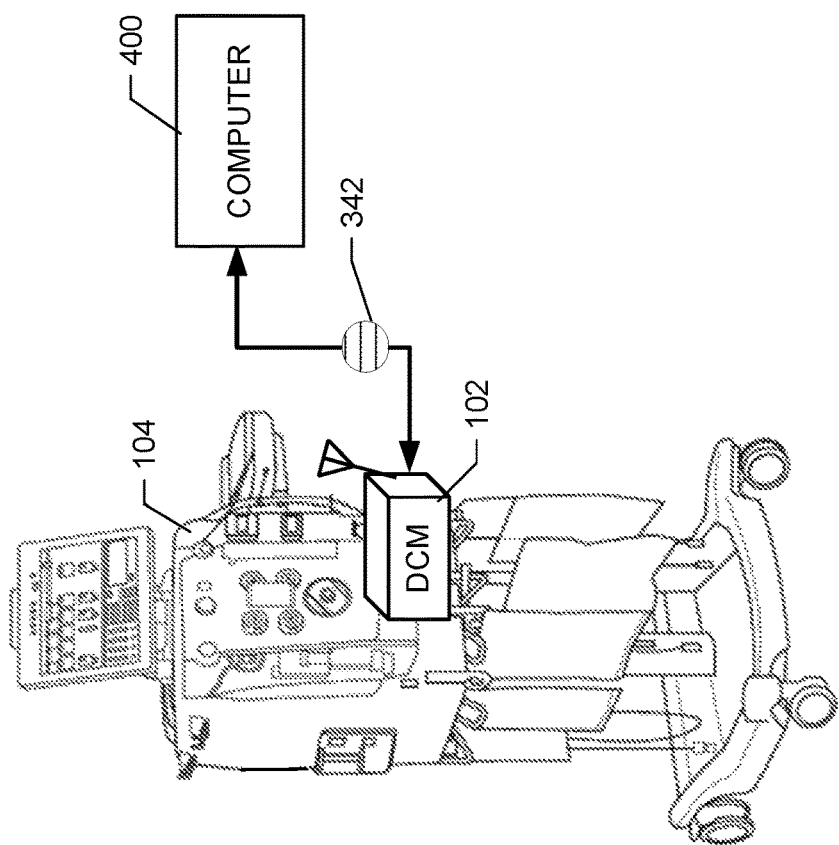

FIG. 4 is a diagram showing the configuration file 342 of FIG. 3 being installed on the DCM 102 via the computer 400, according to an example embodiment of the present disclosure. In this example, the computer 400 connects directly to the DCM 102 via an Ethernet, serial, or USB connection. The computer 400 may be operated by a hospital technical or technical associated with the manufacturer of the medical device 104.

After connecting, the DCM 102, via the configuration file manager 350, launches an interface for display on the computer 400. During this time, an operator of the computer 400 may edit and/or enter information into fields of the user interface related to configuration, network, software, and/or security. Further, the computer 400, via the configuration file manager 350 is configured to enable an operator to specify parameters or attributes of a configuration file 342. After the parameters and/or attributes are specified, the computer 400 transmits the configuration file 342 to the DCM 102. The configuration manager 350 receives the configuration file 342 and provisions or otherwise configures the DCM 102 accordingly.

Figure 5:
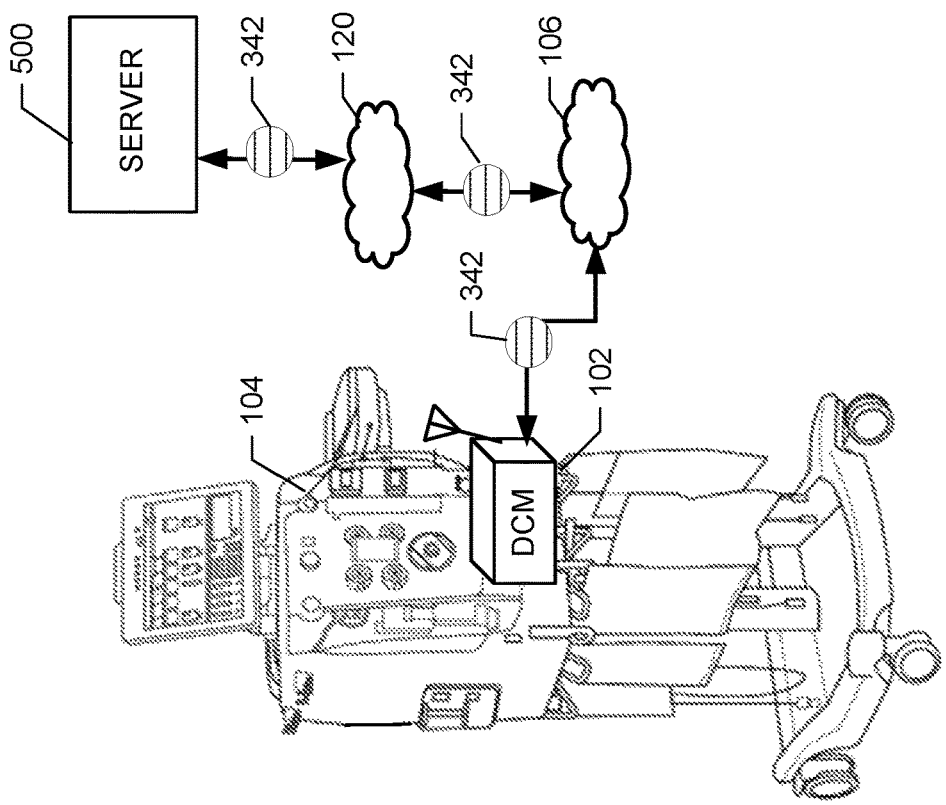
FIGS. 4 and 5 are diagrams that are illustrative as to how a configuration file is installed on the DCM of FIGS. 1 to 3, according to example embodiments of the present disclosure.

FIG. 5 shows a diagram where a server 500 installs the configuration file 342 on the DCM 102. In this example, the DCM 102 may be configured at a time of manufacture with an IP address of the server 500. The DCM 102 may also be configured with credentials and/or network settings for accessing the medical network 106 and/or information related to the medical device 104, such as device type. After the DCM 102 is powered, the DCM 102 transmits a request message to the server 500 requesting the configuration file 342. The request message may include authentication and/or validation information and/or an IP address of the DCM 102. The server 500 may store one or more different types of configuration files based on hospital network and/or local configuration preferences. The server 500 determines which configuration file is assigned to the DCM 102, based for example on a type of the medical device 104, the medical network 106, etc.

In response, after validating, the server 500 transmits the selected configuration file 342 to the DCM 102 via the external network 120 and the medical network 106. The DCM 102 receives the configuration file 342, which is used by the configuration file manager 350 of FIG. 3 to provision or otherwise configure the DCM 102. The configuration shown in FIG. 5 enables automatic configuring of the DCM 102 without a technician or direct connection to a computer. In some embodiments, the server 500 may include the analytics server 122 of FIGS. 1 to 3.

Figure 6:
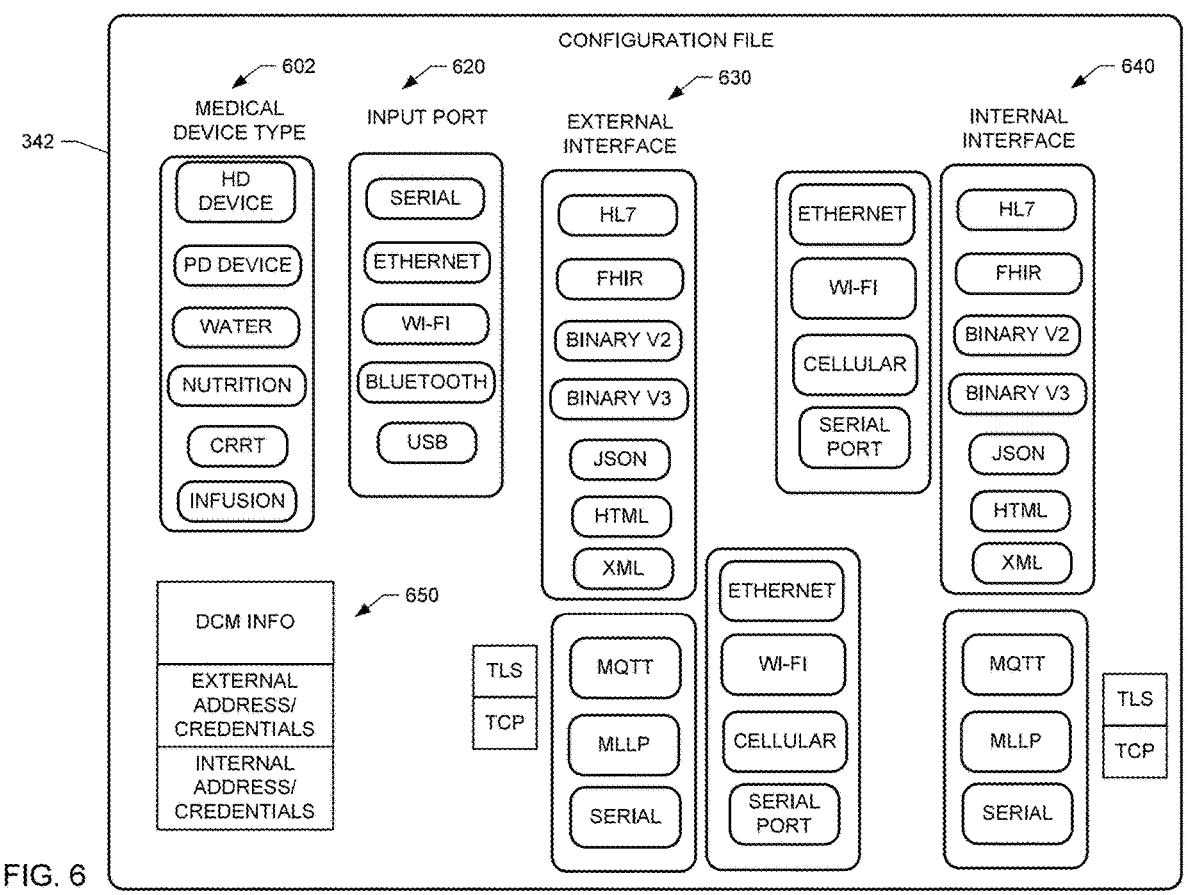
FIG. 6 is a diagram that is illustrative of the configuration file of FIGS. 4 and 5, according to an example embodiment of the present disclosure.

FIG. 6 shows a diagram that is illustrative of the parameters and/or attributes of the configuration file 342 that are selectable by an operator at the computer 400 of FIG. 4 or specified by the server 500 of FIG. 5, according to an example embodiment of the present disclosure. The configuration file 342 includes a parameter for medical device type 602. Selection of a medical device type provides an indication of a type and/or format of medical device data that is to be received. Selection of the medical device type parameter 602 may also cause the DCM 102 to install one or more drivers for processing data from that medical device type. It should be appreciated that the drivers may be stored on the DCM 102 and only installed when the corresponding device type parameter is selected.

The configuration file 342 also includes an input port type parameter 620. Selection of the input port type parameter 620 provides an indication as to which input ports of the DCM 102 are to be provisioned and/or activated. The DCM 102 may also install one or more drivers for the selected input port that specify how data from the medical device is converted, for example, in to a standardized JSON format. The configuration file 342 further includes parameters for the external interface 630 and parameters for the internal interface 640. This includes a data conversion type, a connection protocol, and/or an encryption-data protection protocol. This also includes a selection of one or more hardware output ports of the DCM 102 that should be provisioned and/or activated.

The configuration file 342 further includes parameters for DCM information 650, such as identification information, IP or network address, snapshot period, memory device persistence information, health statistics to monitor, etc. The DCM information parameters 650 may further include external address and/or credentials for accessing the analytics server 122 and internal address and/or credentials for accessing the EMR server 108.

In some embodiments, the configuration file manager 350 may display an interface that is similar to the parameters shown in FIG. 6. A user may select a parameter simply by selecting the corresponding button or entering information into a displayed field. In other embodiments, the configuration file may be text based, XML-based, and/or JSON-based, with the parameters being specified in certain sections of the file or identified by relevant data labels/fields. It should be appreciated that the configuration file 342 enables data transmission to an external server from virtually any medical device type in any desired format without having to make changes to a medical device or network infrastructure.

Figure 7:
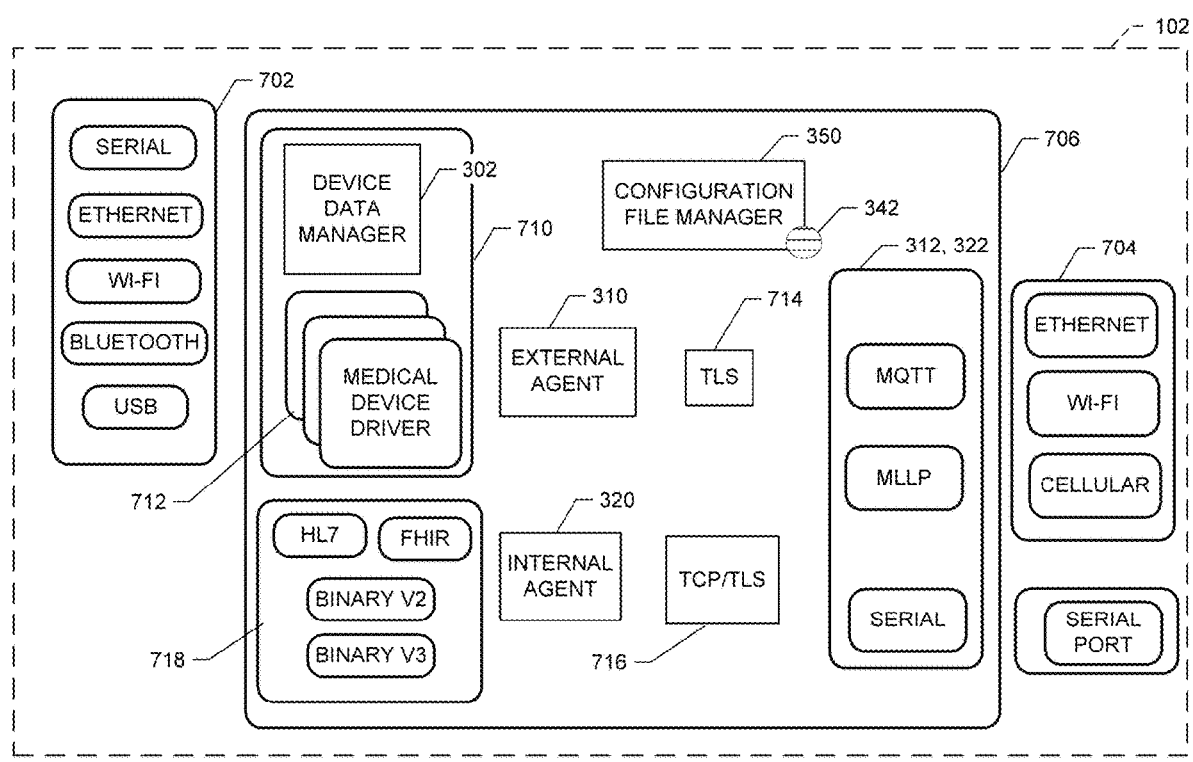
FIG. 7 is a diagram of the DCM of FIGS. 1 to 3 including input ports, output ports, and a processor that includes one or more applications described above in connection with FIG. 3 for processing medical device data, according to an example embodiment of the present disclosure.

FIG. 7 is a diagram of the DCM 102 including input ports 702, output ports 704, and a processor 706 that includes one or more applications described above in connection with FIG. 3 for processing medical device data, according to an example embodiment of the present disclosure. In the illustrated example, the input ports 702 are operational with the device data manager 302 to communicatively couple to a medical device 104. The inputs ports 702 can include one or more serial ports, Ethernet ports, Wi-Fi ports, Bluetooth® ports, or USB ports. It should be appreciated that the DCM 102 may include fewer ports. The configuration file 342 specifies which of the ports are activated for communication with the medical device 104, including installation of the appropriate drivers.

Similarly, the DCM 102 includes output ports 704 for connection to the analytics server 122 and the EMR server 108 via the hospital network 108. In the illustrated example, the output ports 704 are operational with the interfaces 312 and 322 to communicatively couple to the analytics server 122 and the EMR server 108. The output ports 704 can include one or more serial ports, Ethernet ports, Wi-Fi ports, and/or cellular ports. It should be appreciated that the DCM 102 may include fewer or more output ports. The configuration file 342 specifies which of the ports are activated for communication with the medical device 104, including installation of the appropriate drivers.

The example processor 706 specifies one or more instructions that perform the operations described in connection with FIG. 3. The processor 706 includes an input module 710 that includes the device data manager 302 and medical device drivers 712. The example device drivers 712 are installed based on which type of medical device 104 is used with the DCM 102. Each driver includes instructions regarding how the data from the medical device is formatted or structured, which enables the device data manager 302 to identify the different data types for patient de-identification or inclusion in the first and second data streams or subsets 316/326.

The example processor 706 also includes the external agent 310, described above, and an encryption module 714 that is operational with the interface 312. The processor 706 further includes the internal agent 320 and another encryption module 716 that is operational with the interface 322. Additionally, the processor 706 includes the configuration file manager 350 for configuring the DCM 102 as specified by a configuration file 342.

The processor 706 moreover includes a data conversion module 718. The example data conversion module 718 is configured to convert medical device data from a first format to a second format, as specified by the configuration file 342. The different data types of the data conversion module 718 define how data is converted from different formats into the specified second format, such as HL7, binary v2, binary v3, and/or FHIR. In some embodiments, the module 718 may include sections for JSON, XML, HTTP, HTML, etc.

The example DCM 102 of FIG. 7 may be configured as an IoT agent that provides secure, bi-directional connectivity from the DCM to the analytics server 122 by leveraging an IoT framework. The DCM 102 may use the IoT framework for device management, configuration, security, and transmission of connectivity health statistics. In some examples, the DCM 102 is configured with an IoT device shadow for the analytics server 122 for conveying the de-identified first data stream or subset 318 and/or the log/health data 319.

The processor 706 may comprise digital and analog circuitry structured as a microprocessor, application specific integrated circuit ("ASIC"), controller, etc. For example, the processor 106 may include a Digi ConnectCore® 6UL module, which has a NXP i.MX6UL-2, Cortex-A7 528 MHz CPU and 256 MB/1 GB NAND and DDR3 flash drives. The DCM 102 also includes an 802.11a/b/g/n/ac Wi-Fi radio and a Bluetooth® 4.2 radio connected to the corresponding input ports 702 and/or output ports 704. The processor 106 of the DCM 102 may be configured to operate with a Yocto Linux operating system and contains drivers for the Digi chipset. The processor 106 may operate a connectivity application that enables users to manage network and configuration settings via the configuration file manager 350. The connectivity application also permits the DCM 102 to receive remotely provided software and firmware updates.

III. EXAMPLE DCM CONFIGURATION PROCEDURE

Figure 8:
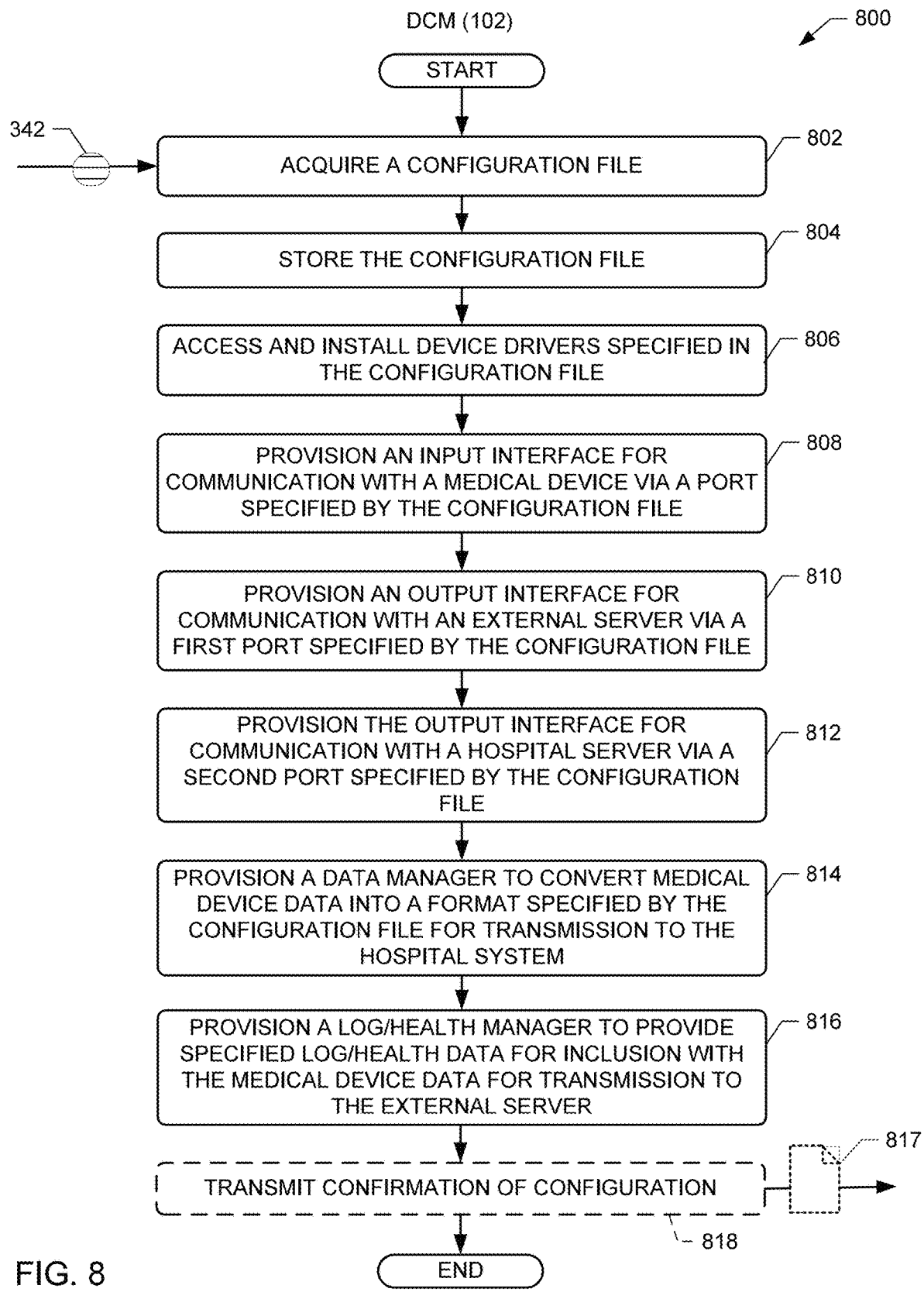
FIG. 8 is a flow diagram of an example procedure for configuring the DCM of FIGS. 1 to 5 and 7 with a configuration file, according to an example embodiment of the present disclosure.

FIG. 8 is a flow diagram of an example procedure 800 for configuring the DCM 102 with a configuration file 342, according to an example embodiment of the present disclosure. Although the procedure 800 is described with reference to the flow diagram illustrated in FIG. 8, it should be appreciated that many other methods of performing the steps associated with the procedure 800 may be used. For example, the order of many of the blocks may be changed, certain blocks may be combined with other blocks, and many of the blocks described may be optional. In an embodiment, the number of blocks may be changed. Further, the step of transmitting a confirmation of a reception of a configuration file 342 may be omitted. The actions described in the procedure 800 are specified by one or more instructions and may be performed among multiple devices including, for example, the DCM 102, the computer 400, and/or the server 500.

The example procedure 800 begins in FIG. 8 when the DCM 102 receives or otherwise acquires a configuration file 342 (block 802). In some embodiments, the configuration file 342 may be created locally at the DCM 102 via a user interface provided by the configuration file manager 350. After acquiring, the DCM 102 stores the configuration file (block 804). The DCM 102 next reads the configuration file 342 to determine which parameters/attributes are specified. Based on the specified parameters/attributes, the DCM 102 accesses and installs the corresponding device drivers for processing data from a specified medical device type (block 806).

The example DCM 102 also provisions one or more input ports of an input interface for communication with a medical device 104 based on the specified parameters/attributes of the configuration file 342 (block 808). The example DCM 102 further provisions one or more output ports of an output interface for communication with the analytics server 122 based on the specified parameters/attributes of the configuration file 342 (block 810). Additionally, the example DCM 102 provisions one or more output ports of the output interface for communication with the EMR server 108 based on the specified parameters/attributes of the configuration file 342 (block 812). Provisioning the input/output ports may include activating identified input and output ports and installing any related drivers.

In addition to above, the DCM 102 provisions a data manager to covert medical device data from a medical device into a format specified by the configuration file 342 for transmission to the EMR server 108 (block 816). In some instances, the DCM 102 provisions the data manager to convert medical device data into a standardized format for processing by the analytics server 122. The DCM 102 may then complete the configuration process by transmitting a confirmation message 817 that is indicative of the configuration to, for example, the computer 400 or the server 500 of FIGS. 4 and 5, respectively (block 818). The example procedure 800 then ends and the DCM 102 is ready to process medical device data.

IV. EXAMPLE DCM MEDICAL DEVICE DATA PROCESSING PROCEDURE

Figure 9:
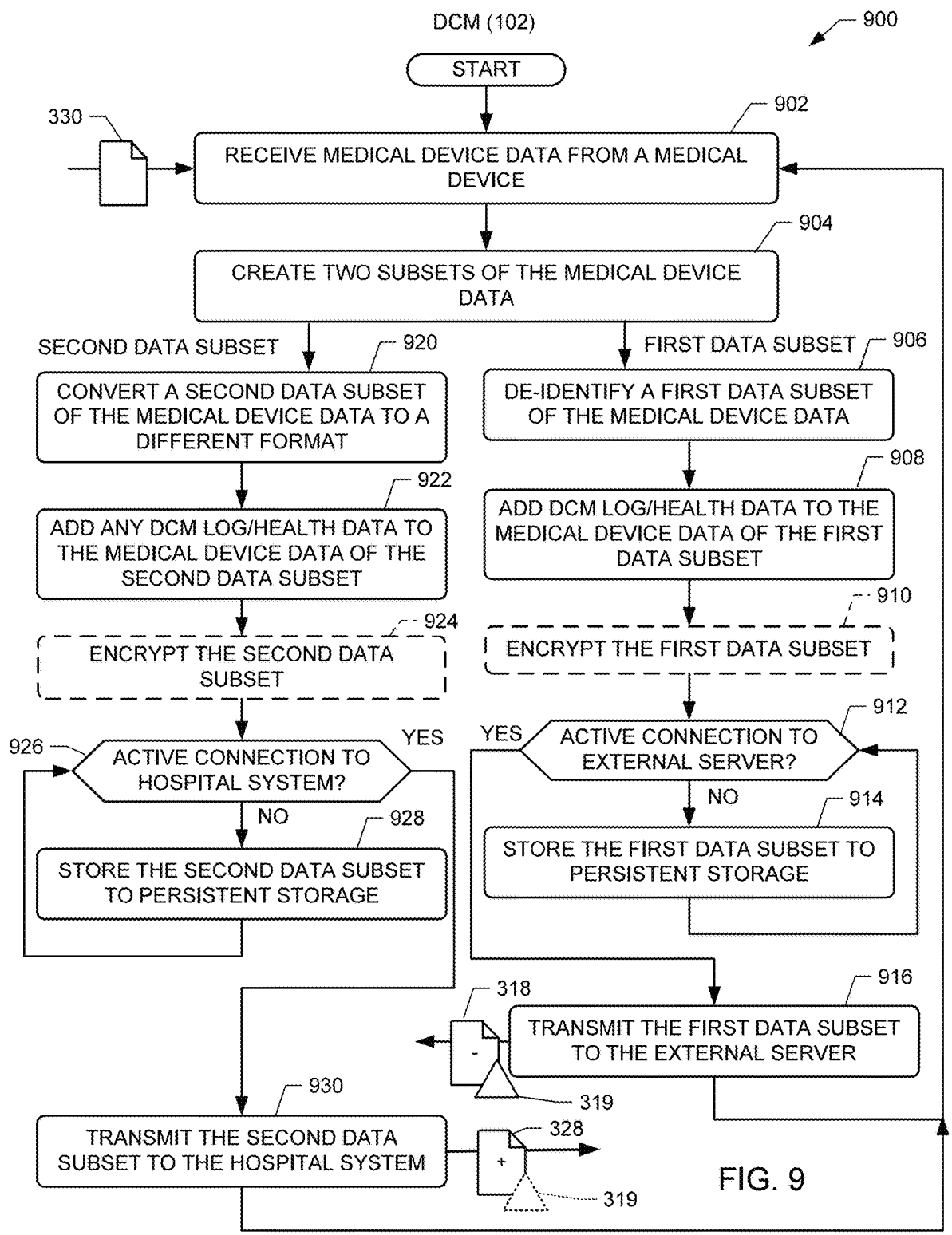
FIG. 9 is a flow diagram of an example procedure for processing medical device data using the DCM of FIGS. 1 to 5 and 7, according to an example embodiment of the present disclosure.

FIG. 9 is a flow diagram of an example procedure 900 for processing medical device data with the DCM 102, according to an example embodiment of the present disclosure. Although the procedure 900 is described with reference to the flow diagram illustrated in FIG. 9, it should be appreciated that many other methods of performing the steps associated with the procedure 900 may be used. For example, the order of many of the blocks may be changed, certain blocks may be combined with other blocks, and many of the blocks described may be optional. In an embodiment, the number of blocks may be changed. Further, the step of encrypting data subsets may be omitted. The actions described in the procedure 900 are specified by one or more instructions and may be performed among multiple devices including, for example, the DCM 102, the medical device 104, the analytics server 122, and/or the EMR server 108.

The example procedure 900 begins when the DCM 102 receives medical device data 330 from a communicatively coupled medical device 104 (block 902). The DCM 102 records a snapshot of the received data based on a periodic interval and creates two separate data streams or subsets (block 904). In some instances, the same medical device data is used for each subset. In other instances, the data subsets may include different and some of the same medical device data.

For a first data stream or subset, the DCM 102 de-identifies the data to create de-identified data 318 (block 906). This includes removing any data that may be used to identify a patient. In some instances, patient identifiers are replaced with session identifiers and/or a random character set. The DCM 102 then adds log/health data 319 to the de-identified data 318 (block 908). The DCM 102 may then encrypt the de-identified data 318 and/or the log/health data (block 910).

The DCM 102 then checks if a connection to the analytics server 122 exists (block 912). In some instances, the DCM 102 may use a Message Queuing Telemetry Transport ("MQTT") messaging protocol to check a connection status. If a connection does not exist, the DCM 102 stores one or more encrypted messages with the de-identified data 318 and/or the log/health data 319 to a persistent memory device (block 914). The DCM 102 continues to store subsequent encrypted messages until a data connection is detected. Once a data connection is detected, the DCM 102 transmits the encrypted messages including the de-identified data 318 and/or the log/health data 319 to the analytics server 122 via one or more networks 106, 120 (block 916). The example procedure 900 then returns to block 902 for processing newly received medical device data.

For the second stream or subset of medical device data, the DCM 102 converts the data into a format that is specified for the EMR server 108 (block 920). This may include converting medical device data in a JSON format, an HL7 format, a binary version ⅔ format, an FHIR format, an XML format, and/or an HTTP format. The DCM 102 may then add log/health data 319 to the converted data 328 (block 922). The DCM 102 may then encrypt the converted data 328 and/or the log/health data 319 (block 924).

The DCM 102 then checks if a connection to the EMR server 108 exists (block 926). In some instances, the DCM 102 may use a MQTT messaging protocol or a Minimum Lower Layer Protocol ("MLLP") to check a connection status. If a connection does not exist, the DCM 102 stores one or more encrypted messages with the converted data 328 and/or the log/health data 319 to a persistent memory device (block 928). The DCM 102 continues to store subsequent encrypted messages until a data connection is detected. Once a data connection is detected, the DCM 102 transmits the encrypted messages including the converted data 328 and/or the log/health data 319 to the EMR server 108 via the medical network 106 and/or a serial connection (block 930). The example procedure 900 then returns to block 902 for processing newly received medical device data.

V. CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A digital communication apparatus comprising:
   an input interface configured for communicative coupling to a medical device, the input interface including a serial input port, an Ethernet input port, and a wireless input port;
   an output interface configured for communicative coupling to a medical network, the output interface including at least one of a serial output port, an Ethernet output port, or a wireless output port;
   a memory device configured to store at least one configuration file and drivers for the input and output ports; and a processor communicatively coupled to the input interface, the output interface, and the memory device, the processor configured to:
receive a configuration file from an administration computer via the output interface, the configuration file specifying one of the input ports of the input interface and at least one output port of the output interface, a first data format, and a second data format,
store the configuration file to the memory device,
identify, as specified by the configuration file, the input port as one of the serial input port, the Ethernet input port, or the wireless input port and the at least one output port as one of the serial output port, the Ethernet output port, or the wireless output port,
install drivers for the identified input and output ports specified by the configuration file,
provision the input interface with the specified input port to receive medical data from the medical device in the first data format, and
provision the output interface with the at least one specified output port to transmit at least some of the received medical data using the first data format and the second data format.

2. The apparatus of claim 1, wherein the processor is configured to:
receive the medical data in the first format from the medical device via the input interface;
select a first subset of the medical data for transmission in the first data format via the output interface via one of the output ports as specified by the configuration file;
convert a second subset of the medical data to the second data format; and
transmit the second subset of the medical data in the second data format for transmission via the same or a different output port as specified by the configuration file.

3. The apparatus of claim 2, wherein the first subset of the medical data is the same as the second subset of the medical data.

4. The apparatus of claim 2, wherein the output interface provides for communicative coupling to at least one of an electronic medical record ("EMR") server, a middleware server, or an integration engine via the medical network, and
wherein the processor is configured to transmit the second subset of the medical data in the second data format to the at least one of the EMR server, the middleware server, or the integration engine using the same or the different output port as specified by the configuration file.

5. The apparatus of claim 2, wherein the at least one of the Ethernet input port and the wireless input port provide for communicative coupling to a remote server that is external to the medical network, and
wherein the processor is configured to transmit the first subset of the medical data in the first data format to the remote server using the at least one of the Ethernet input port or the wireless input port.

6. The apparatus of claim 2, wherein the processor includes a first connectivity agent and uses a messaging protocol for transmission of the first subset of the medical data in the first data format.

7. The apparatus of claim 6, wherein the messaging protocol includes a Message Queuing Telemetry Transport ("MQTT") publish-subscribe network protocol.

8. The apparatus of claim 2, wherein the configuration file specifies a first destination network address that is to receive the first subset of the medical data in the first data format, and specifies a second destination network address that is to receive the second subset of the medical data in the second data format, and
wherein the first destination network address is associated with a network domain that is external to the medical network and the second destination network address is associated with a network domain that includes the medical network.

9. The apparatus of claim 2, wherein the processor is configured to:
generate log data and health data;
include the log data and the health data with the first subset of the medical data for transmission in the first data format via the output interface via one of the output ports as specified by the configuration file;
convert the log data to the second data format; and
include the log data with the second subset of the medical data for transmission via the same or the different output port as specified by the configuration file.

10. The apparatus of claim 9, wherein the log data includes at least one of an identification of a medical device type, an identification of a medical device serial number, a time stamp from which the received medical data was generated by the medical device or received by the processor from the medical device, an identifier of the apparatus, a timestamp for the first subset of the medical data, or a monotonic time stamp, and
wherein the health data includes information related to the memory device, CPU usage information, network connectivity information, process/thread information, or information related to software operated by the processor for processing the first and second subsets of the medical data for transmission.

11. The apparatus of claim 2, wherein the processor is configured to at least one of:
anonymize patient information included within the first subset of the medical data before transmission, or
encrypt the first subset of the medical data before transmission.

12. The apparatus of claim 2, wherein the processor is configured to:
receive a stream of the medial data;
create a snapshot of the medical data at periodic intervals; and
provide the snapshot of the medical data as at least one of the first subset of the medical data or the second subset of the medical data.

13. The apparatus of claim 12, wherein the periodic intervals have a period between five seconds and sixty seconds.

14. The apparatus of claim 12, wherein the processor is configured to:
use event tracking to identify changes to the medical data between snapshots; and
include only the changed medical data from a previous snapshot as at least one of the first subset of the medical data or the second subset of the medical data.

15. The apparatus of claim 1, wherein the configuration file specifies a type of the medical device and that the medical data to be received from the medical device is provided in the first data format.

16. The apparatus of claim 15, wherein the type of the medical device includes at least one of a continuous renal replacement therapy ("CRRT") machine, a peritoneal dialysis machine, a hemodialysis machine, a water purification machine, or a nutrition compounding machine.

17. The apparatus of claim 1, wherein the first data format includes JavaScript Object Notation ("JSON"), Hypertext Transfer Protocol ("HTTP"), or a binary protocol.

18. The apparatus of claim 1, wherein the second data format includes a Health-Level 7 ("HL7") protocol, a Fast Healthcare Interoperability Resources ("FHIR") protocol, or a binary protocol.

19. The apparatus of claim 1, wherein the wireless input port includes at least one of a Wi-Fi input port and a Bluetooth® input port and the wireless output port includes at least one of a Wi-Fi output port or a cellular output port.

20. The apparatus of claim 1, wherein the medical data includes at least one of:
- event information comprising transitions between fill, dwell, and drain phase of a dialysis cycle;
- alarm information;
- treatment programming information; or
- treatment information comprising an estimated fill rate, a drain rate, and an amount of ultrafiltration removed.

* * * * *